United States Patent [19]

Krämer et al.

[11] Patent Number: 4,622,335

[45] Date of Patent: Nov. 11, 1986

[54] FUNGICIDAL HYDROXYETHYLAZOLYL-OXIME DERIVATIVES

[75] Inventors: Wolfgang Krämer, Wuppertal; Karl H. Büchel, Burscheid; Graham Holmwood, Wuppertal; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 649,464

[22] Filed: Sep. 11, 1984

[30] Foreign Application Priority Data

Sep. 26, 1983 [DE] Fed. Rep. of Germany ....... 3334781
Feb. 27, 1984 [DE] Fed. Rep. of Germany ....... 3407005

[51] Int. Cl.$^4$ ............... A01N 43/50; A01N 43/653; C07D 233/60; C07D 249/08
[52] U.S. Cl. .................... 514/383; 514/184; 514/399; 548/101; 548/262; 548/341; 549/548; 549/552; 549/559; 564/256
[58] Field of Search ............ 548/101, 262, 341; 514/184, 383, 399

[56] References Cited

U.S. PATENT DOCUMENTS 3,974,174 8/1976 Buchel et al. ................ 548/262
4,496,388 1/1985 Clough ........................ 548/336

FOREIGN PATENT DOCUMENTS 0114487 8/1984 European Pat. Off. ........... 548/262
0114567 8/1984 European Pat. Off. ........... 548/262
0117578 9/1984 European Pat. Off. ........... 548/262

Primary Examiner—Alton D. Rollins
Attorney, Agent, or Firm—Sprung Horn Kramer & Woods

[57] ABSTRACT

Fungicidally active novel hydroxyethylazolyl-oxime derivatives of the formula

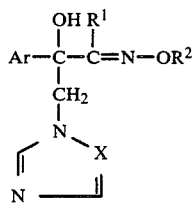

in which Ar is optionally substituted aryl,
$R^1$ is hydrogen or alkyl,
$R^2$ is hydrogen, alkyl, alkenyl, alkinyl, optionally substituted aralkyl or optionally substituted cycloalkylalkyl, and
X is a nitrogen atom or the CH group, and addition products thereof with acids and metal salts.

12 Claims, No Drawings

FUNGICIDAL HYDROXYETHYLAZOLYL-OXIME DERIVATIVES

The present invention relates to new hydroxyethylazolyl-oxime derivatives, several processes for their preparation and their use as fungicides.

It has already been disclosed that certain hydroxyethylazole derivatives, such as, for example, 2-(4-chlorophenoxymethyl)-3,3-dimethyl-1-(imidazol-1-yl)-butan-2-ol, have good fungicidal properties (application Ser. No. 549,867, filed Nov. 8, 1983, now pending corresponding to German Offenlegungsschrift No. 3,018,866). The action of these compounds is, however, not always fully satisfactory when they are used in low quantities and concentrations.

New hydroxyethylazolyl-oxime derivatives of the general formula (I)

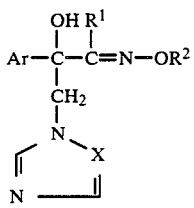

(I)

in which
Ar represents optionally substituted aryl,
$R^1$ represents hydrogen or alkyl,
$R^2$ represents hydrogen, alkyl, alkenyl, alkinyl, optionally substituted aralkyl or optionally substituted cycloalkylalkyl and
X represents a nitrogen atom or the CH group,
and acid addition salts and metal salt complexes thereof, have been found.

It has furthermore been found that the hydroxyethylazolyl-oxime derivatives of the formula (I) are obtained when (a) hydroxyethylazolyl-keto derivatives of the formula (II)

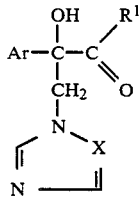

(II)

in which
Ar, $R^1$ and X have the abovementioned meaning, it also being possible for the keto group to be in a chain-like or cyclic acetal or ketal structure,
are reacted with hydroxylamine derivatives of the formula (III)

$$H_2N-O-R^2 \quad (III)$$

in which
$R^2$ has the abovementioned meaning,
in the presence of a diluent, and if appropriate, furthermore, (b) the hydroxyethylazolyl-oxime derivatives, obtained according to process (a), of the formula (Ia) (that is to say compounds of the general formula (I) in which $R^2$ represents hydrogen)

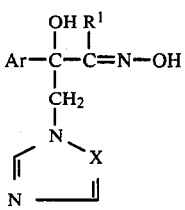

(Ia)

in which
Ar, $R^1$ and X have the abovementioned meaning, are reacted with halides of the formula (IV)

$$Hal-R^3 \quad (IV)$$

in which
Hal represents chlorine, bromine or iodine and
$R^3$ has the meanings of $R^2$, with the exception of hydrogen,
in the presence of a diluent and if appropriate in the presence of a base; or (c) oxiranes of the general formula (V)

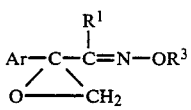

(V)

in which
Ar, $R^1$ and $R^3$ have the abovementioned meaning, are reacted with azoles of the formula (VI)

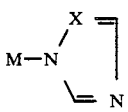

(VI)

in which
X has the abovementioned meaning and
M represents hydrogen or an alkali metal, in the presence of a diluent and if appropriate in the presence of a base.

If appropriate, an acid or a metal salt can then be added on to the compounds of the formula (I) thus obtained.

The compounds of the formula (I) can be in the form of two geometrical isomers (syn- and anti-form), they occur predominantly in the form of mixtures of varying combinations of both forms. The compounds according to the invention, of the general formula (I), surprisingly exhibit better fungicidal action than the hydroxyethylazole derivatives known from the prior art.

The active compounds according to the invention thus represent an enrichment of the art.

Formula (I) provides a general definition of the hydroxyethylazolyl-oxime derivatives according to the invention. Preferably, in this formula:

Ar represents naphthyl, or represents phenyl which is optionally monosubstituted or polysubstituted by identical or different substituents, substituents which may be mentioned being: halogen, alkyl with 1 to 4 carbon atoms, alkoxy and alkylthio with in each case 1 or 2 carbon atoms, nitro, halogenoalkyl, halogenoalkoxy and halogenoalkylthio with in each case 1 or 2 carbon atoms and 1 to 5 identical or different halogen atoms, such as, preferably, fluorine and chlorine atoms, alkoxyiminomethyl with 1 to 4 carbon atoms in the alkyl part, alkenyloximinomethyl with 2 to 4 carbon atoms in the alkenyl part, and phenyl, phenoxy, benzyl and benzyloxy, each of which is optionally substituted by halogen and/or alkyl with 1 or 2 carbon atoms;

$R^1$ represents hydrogen or straight-chain or branched alkyl with 1 to 4 carbon atoms;

$R^2$ represents hydrogen, straight-chain or branched alkyl with 1 to 4 carbon atoms, or alkenyl or alkinyl with in each case 2 to 6 carbon atoms, or represents phenylalkyl which has 1 or 2 carbon atoms in the alkyl part and is optionally monosubstituted or polysubstituted by identical or different substituents, possible substituents on the phenyl being the substituents on phenyl mentioned for Ar, or represents cycloalkylmethyl which has 5 or 6 carbon atoms in the cycloalkyl part and is optionally mono-, di- or tri-substituted by identical or different alkyl radicals with 1 to 3 carbon atoms; and X represents a nitrogen atom or the CH group.

Particularly preferred compounds of the formula (I) are those in which

Ar represents naphthyl, or represents phenyl which is optionally mono-, di- or tri-substituted by identical or different substituents, substituents which may be mentioned being: fluorine, chlorine, methyl, trifluoromethyl, trifluoromethoxy, trifluoromethylthio, hydroxyiminomethyl, methoximinimethyl, ethoximinomethyl and allyloximinomethyl, and phenyl, phenoxy, benzyl and benzyloxy, each of which is optionally substituted by chlorine and/or methyl;

$R^1$ represents hydrogen or straight-chain alkyl with 1 to 4 carbon atoms;

$R^2$ represents hydrogen, straight-chain alkyl with 1 to 4 carbon atoms, allyl, butenyl or propargyl, or represents benzyl which is optionally mono- or di-substituted by identical or different substituents from the group comprising fluorine, chlorine, methyl, trifluoromethyl and trifluoromethoxy, or represents cyclohexylmethyl which is optionally substituted by methyl or ethyl; and X represents a nitrogen atom or the CH group.

Addition products of acids and those hydroxyethylazolyl-oxime derivatives of the formula (I) in which the substituents Ar, $R^1$, $R^2$ and X have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II to IV and of sub-groups I and II and IV to VIII and those hydroxyethylazolyl-oxime derivatives of the formula (I) in which the substituents Ar, $R^1$, $R^2$ and X have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from those acids which lead to physiologically acceptable addition products. In this connection, particularly preferred acids of this type are the hydrogen halide acids, such as, for example, hydrochloric acid and hydrobromic acid, and nitric acid and sulphuric acid.

The following compounds of the general formula (I)

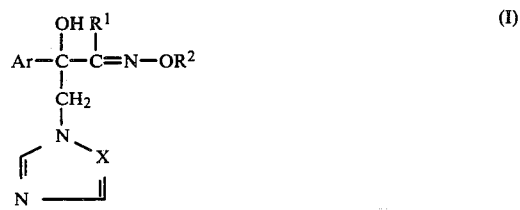

may be mentioned specifically, in addition to the compounds mentioned in the preparation examples (X represents either a nitrogen atom or the CH group):

| Ar | $R^1$ | $R^2$ |
|---|---|---|
|  | H | $CH_3$ |
| 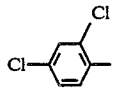 | H | $C_2H_5$ |
| 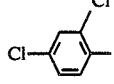 | H | $C_4H_9-n$ |
| 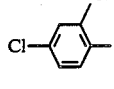 | H | 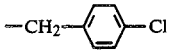 |
| 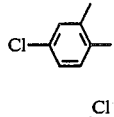 | $C_4H_9-n$ | H |
| 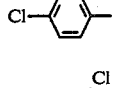 | $C_4H_9-n$ | $CH_3$ |
| 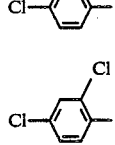 | $C_3H_7-n$ | $CH_3$ |
|  | H | $C_3H_7$ |
| 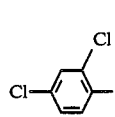 | H | $-CH_2-CH=CH_2$ |
|  | H | $-CH_2-CH-CH=CH_2$ |

-continued

| Ar | R¹ | R² |
|---|---|---|
| 2,4-dichlorophenyl | H | —CH₂—cyclohexyl |
| 2,4-dichlorophenyl | H | —CH₂—C≡CH |
| 2,4-dichlorophenyl | CH₃ | CH₃ |
| 2,4-dichlorophenyl | CH₃ | C₂H₅ |
| 2,4-dichlorophenyl | CH₃ | C₃H₇ |
| 2,4-dichlorophenyl | CH₃ | C₄H₉—n |
| 2,4-dichlorophenyl | CH₃ | C₄H₉—sec. |
| 2,4-dichlorophenyl | CH₃ | —CH₂—CH=CH₂ |
| 2,4-dichlorophenyl | CH₃ | —CH₂—CH₂—CH=CH₂ |
| 4-chlorophenyl | H | —CH₂—cyclohexyl |
| 2,4-dichlorophenyl | CH₂ | —CH₂—C≡CH |
| 2,4-dichlorophenyl | H | —CH₂—C₆H₄—Cl (4) |
| 2,4-dichlorophenyl | H | —CH₂—(2,6-dichlorophenyl) |
| 2,4-dichlorophenyl | H | —CH₂—C₆H₄—CH₃ |
| 2,4-dichlorophenyl | H | —CH₂—(2,4,6-trimethylphenyl) |

-continued

| Ar | R¹ | R² |
|---|---|---|
| 4-chlorobiphenyl | H | CH₃ |
| biphenyl | H | CH₃ |
| 4-chlorophenyl | H | —CH₂—(2,4-dichlorophenyl) |
| 4-chlorophenyl | H | CH₃ |

If, for example, 2-(2,4-dichlorophenyl)-3,3-dimethoxy-2-hydroxy-1-(1,2,4-triazol-1-yl)-propane and O-methyl-hydroxylamine hydrochloride are used as starting substances, the course of process (a) according to the invention can be represented by the following equation:

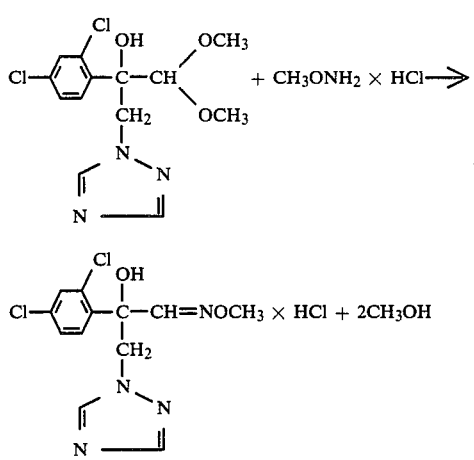

If, for example, 2-(2,4-dichlorophenyl)-2-hydroxy-2-hydroximinomethyl-1-(1,2,4-triazol-1-yl)-ethane and 4-chlorobenzyl chloride are used as starting substances, the course of process (b) according to the invention can be represented by the following equation:

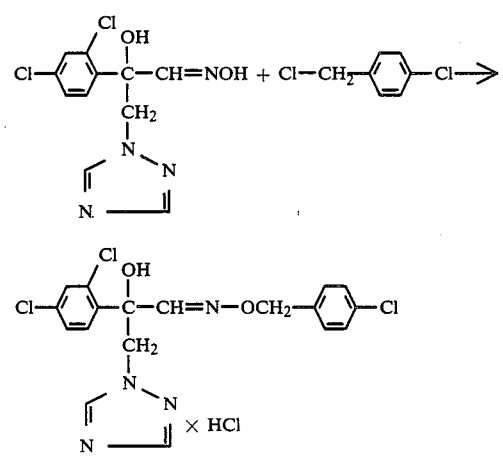

If, for example, 2-(2,4-dichlorophenyl)-2-(1-methoximino-1-butyl)-oxirane and 1,2,4-triazole are used as starting substances, the course of process (c) according to the invention can be represented by the following equation:

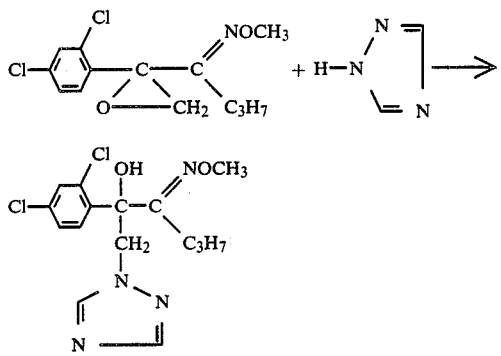

Formula (II) provides a general definition of the hydroxyethylazolyl-keto derivatives to be used as starting substances for carrying out process (a) according to the invention. In this formula, Ar, $R^1$, $R^2$ and X preferably have the meanings which have already been mentioned as preferred for these substituents in connection with the description of the substances of the formula (I) according to the invention.

The hydroxyethylazolyl-keto derivatives of the formula (II) have been described in some cases (compare, for example, European No. 0,078,594); or they are the subject of application Ser. No. 547,807, filed Nov. 1, 1983, now pending, corresponding to German Patent Application No. P 32 42 252 of Nov. 15, 1982; or they can be obtained by the processes described therein, by reacting oxiranes of the formula (VII)

in which
Ar and $R^1$ have the abovementioned meaning, it also being possible for the keto group to be in a chainlike or cyclic acetal or ketal structure,
with azoles of the formula (VI) under the conditions of process (c).

The oxiranes of the formula (VII) have been described in some cases (compare, for example, European No. 0,078,549); or they are the subject of application Ser. No. 547,807, filed Nov. 1, 1983, now pending, corresponding to German Patent Application No. P 32 42 252 of Nov. 15, 1982; or they can be obtained in a generally known manner, by epoxidizing corresponding ketones in the customary manner.

Formula (III) provides a general definition of the hydroxylamine derivatives also to be used as starting substances for carrying out process (a) according to the invention. In this formula, $R^2$ preferably represents the meanings which have already been mentioned as preferred for this substituent in connection with the description of the substances of the formula (I) according to the invention.

The hydroxylamine derivatives of the formula (III) are generally known compounds of organic chemistry.

The hydroxyethylazolyl-oxime derivatives of the formula (Ia) to be used as starting substances in carrying out process (b) according to the invention are compounds according to the invention.

Formula (IV) provides a general definition of the halides also to be used as starting substances for carrying out process (b) according to the invention. In this formula, $R^3$ preferably represents the meanings which have already been mentioned as preferred for $R^2$, with the exception of hydrogen, in connection with the description of the substances of the formula (I) according to the invention.

The halides of the formula (IV) are generally known compounds of organic chemistry.

Formula V provides a general definition of the oxiranes to be used as starting substances in carrying out process (c) according to the invention. In this formula, Ar, $R^1$ and $R^2$ preferably represent the meanings which have already been mentioned as preferred for these substituents in connection with the description of the substances of the formula (I) according to the invention.

The oxiranes of the formula (V) are not yet known. However, they can be obtained in a generally known manner, by reacting the corresponding keto-oxime derivatives of the formula (VIII)

in which
Ar, $R^1$ and $R^3$ have the abovementioned meaning, either
(α) with dimethyloxosulphonium methylide of the formula (IX)

in a manner which is known per se in the presence of a diluent, such as, for example, dimethylsulphoxide, at temperatures between 20° C. and 80° C. (in this context, compare the statements in J. Am. Chem. Soc. 87, 1363–1364 (1965)), or
(β) with trimethylsulphonium methyl-sulphate of the formula (X)

in a manner which is known per se in the presence of an inert organic solvent, such as, for example, acetonitrile, and in the presence of a base, such as, for example, sodium methylate, at temperatures between 0° C. and 60° C., preferably at room temperature (compare also the statements in Heterocycles 8, 397 (1977)).

The keto-oxime derivatives of the formula (VIII) are obtained by reacting corresponding ketones of the formula (XI)

in which
Ar and $R^1$ have the abovementioned meaning, with a nitrosating agent, such as, for example, nitrous acid and esters thereof, in the customary manner and, if appropriate, reacting the resulting keto-oximes of the formula (XII)

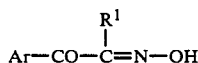

(XII)

in which

Ar and $R^1$ have the abovementioned meaning, with halides of the formula (IV) under the conditions of process (b).

Formula (VI) provides a general definition of the azoles also to be used as starting substances for carrying out process (c) according to the invention. In this formula, X preferably represents the meanings which have already been mentioned for this substituent in the definition of the invention. M preferably represents hydrogen, sodium or potassium.

The azoles of the formula (VI) are generally known compounds of organic chemistry.

Preferred possible diluents for process (a) according to the invention are alcohols and water, or mixtures of the two.

The reaction temperatures can be varied within a substantial range in process (a). In general, the reaction is carried out between 20° C. and 120° C., preferably between 50° C. and 100° C.

In carrying out process (a) according to the invention, 1 to 1.5 mols of hydroxylamine derivative of the formula (III) are preferably employed per mol of the compound of the formula (II). The compounds of the formula (I) are isolated by customary methods.

According to a preferred embodiment of process (a), the hydroxylamine derivatives of the formula (III) are used in the form of their salts, in particular as the hydrochlorides, if appropriate in the presence of an acid-binding agent, such as, for example, sodium acetate.

Possible diluents for the reaction according to process (b) are inert organic solvents. These include, preferably, ethers, such as tetrahydrofuran and dioxane; aromatic hydrocarbons, such as toluene and benzene; in individual cases also chlorinated hydrocarbons, such as chloroform, methylene chloride or carbon tetrachloride; and hexamethylphosphoric acid triamide, acid amides, such as dimethylformamide, and sulphoxides, such as dimethylsulphoxide.

If appropriate, the reaction according to the invention in process (b) is carried out in the presence of a strong base. Strong bases include, preferably, alkali metal amides, hydrides, hydroxides and carbonates, such as, for example, sodium amide, carbonate, hydroxide or hydride and potassium amide, carbonate, hydroxide or hydride, and quaternary ammonium hydroxides and phosphonium hydroxides, such as, for example, tetramethylammonium hydroxide, benzyltrimethylammonium hydroxide or dibenzyl-dimethyl-ammonium hydroxide and tetraphenylphosphonium hydroxide or methyltriphenylphosphonium hydroxide.

The reaction temperatures can be varied within a substantial range in process (b). In general, the reaction is carried out between 20° C. and 150° C., preferably at room temperature. In individual cases, it is advantageous to carry out the reaction at the boiling point of the solvent, for example between 60° C. and 100° C.

In carrying out process (b) according to the invention, 1, to 3 mols of halide of the formula (IV) are preferably employed per mol of the compounds of the formula (Ia). To isolate the end products, the reaction mixture is freed from the solvent, and water and an organic solvent are added to the residue. The organic phase is separated off and the product is worked up and purified in the customary manner.

In a preferred embodiment of process (b), the reaction according to the invention is carried out in a two-phase system, such as, for example, aqueous sodium hydroxide solution or potassium hydroxide solution/toluene or methylene chloride, with addition of 0.01 to 1 mol of a phase transfer catalyst, such as, for example, ammonium or phosphonium compounds, the alcoholates being formed in the organic phase or at the interface and reacting with the halides in the organic phase.

Possible diluents for process (c) according to the invention are organic solvents which are inert under the reaction conditions. These include, preferably, alcohols, such as, for example, ethanol, methoxyethanol or propanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible bases for the reaction according to the invention in process (c) are all the inorganic and organic bases which can customarily be used. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out process (c) according to the invention. In general, the reaction is carried out at temperatures between 0° C. and 200° C., preferably between 60° C. and 150° C.

In carrying out process (c) according to the invention, 1 to 2 mols of azole of the formula (VI) and, if appropriate, 1 to 2 mols of base are preferably employed per mol of oxirane of the formula (V); the end products are isolated in the generally customary manner.

Those acids which have already been mentioned as preferred acids in connection with the description of the acid addition salts according to the invention can preferably be used for the preparation of acid addition salts of compounds of the general formula (I).

The acid addition salts of the compounds of the formula (I) can be obtained in a simple manner by customary salt formation methods, for example by dissolving a compound of the general formula (I) in an inert solvent and adding the acid, for example hydrochloric acid, and they can be isolated in a known manner, for example by filtration, and if appropriate purified by washing with an inert organic solvent.

Those salts of metals which have already been described above can preferably be used for the preparation of metal salt complexes of the compounds of the general formula (I).

The metal salt complexes of the compounds of the general formula (I) can be obtained in a simple manner by customary processes, thus, for example, by dissolving the metal salt in alcohol, for example ethanol, and adding the solution to the compounds of the general formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The compounds exhibit good action, in particular against species of Puccinia and species of Cochliobolus in wheat cultures and against species of Venturia, such as, for example, against *Venturia maequalis*, the pathogen of apple scab. In addition a good action against mildew and *Septoria nodorum* in cereals and against *Pyricularia oryzae* in rice must be mentioned. In the agar plate test the active compounds according to the invention exhibit a broad spectrum of action.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

USE EXAMPLES

In the following examples the compounds indicated below are used as comparative substances:

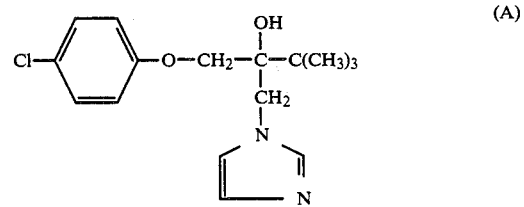

(A)

-continued (B) 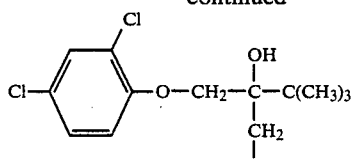

(C) 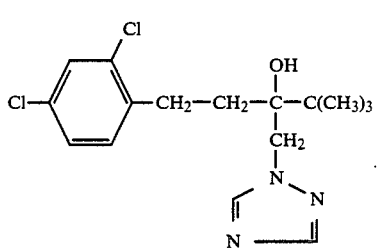

(D) 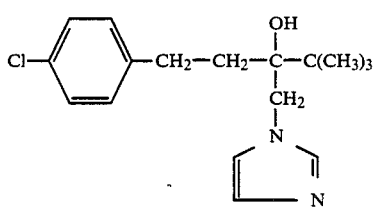

EXAMPLE A

Puccinia Test (wheat)/protective

Solvent: 100 parts by weight dimethylformamide.
Emulsifier: 0.25 parts by weight alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 2, 4 and 6.

EXAMPLE B

*Cochliobulus sativus* test (barley)/protective

Solvent: 100 parts by weight of dimethylformamide.
Emulsifier: 0.25 part by weight of alkylaryl polyglycol ether.

To produce a suitable preparation of active compound 1 part by weight of active compound was mixed with the stated amounts of solvent and emulsifier and the concentrate was diluted with water to the desired concentration.

To test for protective activity young plants were sprayed with the preparation of active compound until dew-moist. After the spray coating had dried on the plants were sprayed with a conidium suspension of *Cochiobolus sativus*. The plants remained in an incubation chamber for 48 hours at 20° C. and at a relative atmospheric humidity of 100%.

The plants were placed in a greenhous at a temperature of about 20° C. and a relative atmospheric humidity of about 80%.

Evaluation was carried out 7 days after the inoculation.

In this test a significantly superior activity compared with the prior art was shown, for example, by the compounds according to the following preparation examples: 2, 4 and 6.

EXAMPLE C

Venturia test (apple)/protective

Solvent: 4.7 parts by weight acetone.
Emulsifier: 0.3 parts by weight alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 2 and 4.

PREPARATION EXAMPLES

Example 1

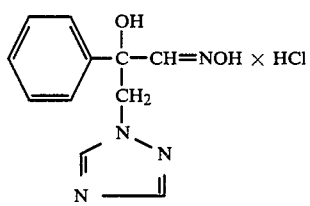

(Process a)

10 g (0.038 mol) of 1,1-dimethoxy-2-hydroxy-2-phenyl-3-(1,2,4-triazol-1-yl)-propane are heated under reflux with 50 ml of water, 5 ml of concentrated hydrochloric acid and 3 g of hydroxylammonium hydrochloride for 15 hours. Saturated sodium bicarbonate solution is then added to the reaction mixture. 100 ml of n-butanol are added to the aqueous phase, the organic phase is then separated off and the aqueous phase is washed twice with 50 ml of butanol each time. The combined butanol phases are washed with 50 ml of water, dried over sodium sulphate and concentrated in vacuo. The residue is taken up in 100 ml of methylene chloride, and 50 ml of diethyl ether saturated with hydrogen chloride are added. The reaction mixture is concentrated and the residue is recrystallized from 100 ml of acetonitrile.

4 g (40% of theory) of 2-hydroxy-2-phenyl-2-(1,2,4-triazol-1-yl-methyl)-acetaldoxime hydrochloride of melting point 178° C. to 180° C. (decomposition) are obtained.

Preparation of the starting substance

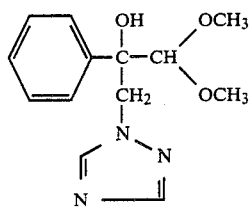

1,1-Dimethoxy-2-hydroxy-2-phenyl-3-(1,2,4-triazol-1-yl)-propane of melting point 85° C. to 86° C. is obtained by the customary reaction of crude 2-dimethoxymethyl-2-phenyl-oxirane with 1,2,4-triazole in the presence of potassium hydroxide.

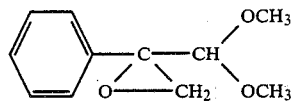

2-Dimethoxymethyl-2-phenyl-oxirane, which is further reacted directly, is obtained by customary reaction of ω-dimethoxyacetophenone with dimethylsulphide/dimethyl sulphate in the presence of potassium tert.-butylate.

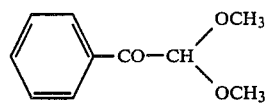

ω-Dimethoxyacetophenone of boiling point 130° C./8 mm Hg is obtained by customary reaction of dimethoxyphenyl-acetaldehyde in methanol with concentrated hydrochloric acid.

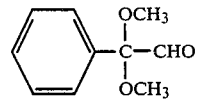

Dimethoxy-phenyl-acetaldehyde, which is further reacted directly, is obtained by customary reaction of ω-dichloroacetophenone with sodium methylate in methanol.

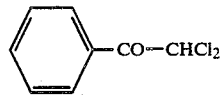

ω-Dichloroacetophenone of boiling point 130° C./12 mm Hg is obtained by customary reaction of acetophenone with sulphuryl chloride.

EXAMPLE 2

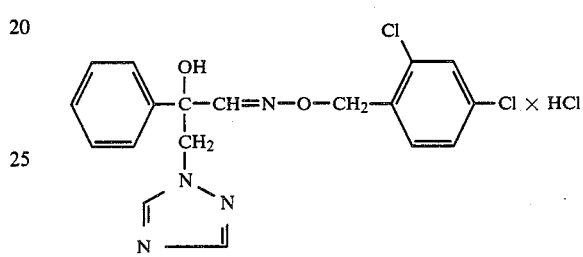

(Process b)

4 g (0.015 mol) of 2-hydroxy-2-phenyl-2-(1,2,4-triazol-1-yl-methyl)-acetaldoxime hydrochloride (Example 1) in 40 ml of toluene are stirred with 40 ml of aqueous sodium hydroxide solution, 1 ml of 50% strength aqueous solution of dimethylbenzylammonium hydroxide and 2.9 g (0.015 mol) of 2,4-dichlorobenzyl chloride at room temperature for 10 hours. The toluene phase is then separated off, washed three times with 100 ml of saturated sodium chloride solution each time, dried over sodium sulphate and concentrated in vacuo. The residue is taken up in diethyl ether, and diethyl ether saturated with hydrogen chloride is added. The reaction mixture is concentrated and the residue is recrystallized from 20 ml of ethanol.

1 g (15.6% of theory) of 3-(2,4-dichlorobenzyloximino)-2-hydroxy-2-phenyl-1-(1,2,4-triazol-1-yl)-propane hydrochloride of melting point 148° C. to 153° C. are obtained.

The following compounds of the general formula (I) can be obtained in a corresponding manner and according to the processes described:

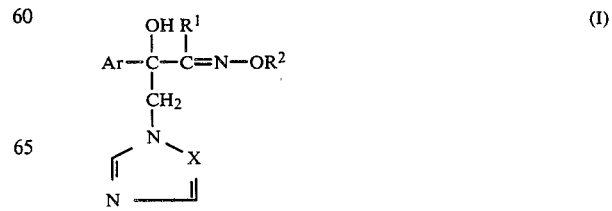
(I)

| Example No. | Ar | R¹ | R² | X | Physical constants |
|---|---|---|---|---|---|
| 3 | 2,4-dichlorophenyl | H | H | N | Oil (× HCl), ¹HNMR$_{CDCl_3/DMSO}$: $\delta = 5.23$ ppm (s), for $-CH_2-$N(triazole); $\delta = 7.43$ ppm (s), for $-CH=N-$ |
| 4 | 2,4-dichlorophenyl | H | $-CH_2-$(2,4-dichlorophenyl) | N | Melting point = 125–30° C. |
| 5 | phenyl | H | $CH_3$ | N | Oil (× HCl), ¹HNMR$_{DMSO}$: $\delta = 4.47$ ppm (s), for $-CH_2-$N(triazole); $\delta = 5.70$ ppm (s), for $-CH=N-$ |
| 6 | phenyl | $CH_3$ | $-CH_2-$(2,4-dichlorophenyl) | N | Melting point = 212–216° C. × ½ NDS |
| 7 | phenyl | $CH_3$ | $-CH_2-$(3,4-dichlorophenyl) | N | melting point = 158–160° C. (× HCl) |
| 8 | phenyl | $CH_3$ | $-CH_2-$(4-chlorophenyl) | N | melting point = 151–157° C. (× HCl) |
| 9 | phenyl | $CH_3$ | $-CH_2-$(2,4-dichlorophenyl) | N | Oil, ¹HNMR$_{CDCl_3}$: $\delta(CH_3) = 1.73/1.76$ ppm (Isomere mixtures in the ratio of 1:3) |
| 10 | 2,4-dichlorophenyl | H | $-CH_2-$(4-chlorophenyl) | N | melting point = 145° C. |
| 11 | phenyl | $CH_3$ | $-CH_2-$(2-methylphenyl) | N | melting point = 168–178° C. (× HCl) |
| 12 | phenyl | $CH_3$ | $-CH_2-$(4-fluorophenyl) | N | melting point = 148–150° C. (× HCl) |

NDS = 1,5-naphthalenedisulphonic acid

It will be understood that the specification and examples are illustrative but not limitative of the present

We claim:
1. A hydroxyethylazolyl-oxime derivative of the formula

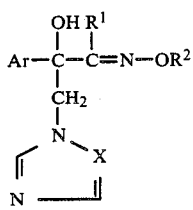

in which
Ar is naphthyl, or is phenyl which is optionally substituted by halogen, alkyl with 1 to 4 carbon atoms, alkoxy or alkylthio with in each case 1 or 2 carbon atoms, nitro, halogenoalkyl, halogenoalkoxy or halogenoalkylthio with in each case 1 or 2 carbon atoms and 1 to 5 identical or different halogen atoms, hydroximinomethyl, alkoximinomethyl with 1 to 4 carbon atoms in the alkyl part, alkenyloximinomethyl with 2 to 4 carbon atoms in the alkenyl part, and/or phenyl, phenoxy, benzyl or benzyloxy, each of which is optionally substituted by halogen and/or alkyl with 1 or 2 carbon atoms,
$R^1$ is hydrogen or alkyl with 1 to 4 carbon atoms, and
$R^2$ is alkyl with 1 to 4 carbon atoms, or alkenyl or alkinyl with in each case 2 to 6 carbon atoms, or is phenylalkyl which has 1 to 2 carbon atoms in the alkyl part and is optionally substituted on the phenyl by the substituents on phenyl mentioned for Ar, or is cycloalkylmethyl which has 5 or 6 carbon atoms in the cycloalkyl part and optionally mono-, di- or tri-substituted by identical or different alkyl radicals with 1 to 3 carbon atoms, and
X is a nitrogen atom or the CH group,
or an addition product thereof with an acid or metal salt.

2. A compound or addition product according to claim 1, in which
Ar is phenyl optionally substituted by halogen, alkyl with 1 to 4 carbon atoms, halogenoalkyl with 1 or 2 carbon atoms and 1 to 5 identical or different halogen atoms, alkoximinomethyl with 1 to 4 carbon atoms in the alkyl part, and/or phenyl,
$R^1$ is hydrogen or alkyl with 1 to 4 carbon atoms,
$R^2$ is alkyl with 1 to 4 carbon atoms or phenylalkyl which has 1 or 2 carbon atoms in the alkyl part and is optionally substituted on the phenyl part by halogen and/or alkyl with 1 to 4 carbon atoms.

3. A hydrochloric acid or 1,5-naphthalene-disulphonic acid addition product of claim 1.

4. A compound or addition product according to claim 1, in which
Ar is naphthyl, or is phenyl which is optionally mono-, di- or tri-substituted by fluorine, chlorine, methyl, trifluoromethyl, trifluoromethoxy, trifluoromethylthio, hydroximinomethyl, methoximinomethyl, ethoximinomethyl, allyloximinomethyl and/or phenyl, phenoxy, benzyl or benzyloxy, each of which is optionally substituted by chlorine and/or methyl,
$R^1$ is hydrogen or alkyl with 1 to 4 carbon atoms, and
$R^2$ is straight-chain alkyl with 1 to 4 carbon atoms, allyl, butenyl or propargyl, or is benzyl which is optionally mono- or di-substituted by fluorine, chlorine methyl, trifluoromethyl and/or trifluoromethoxy, or is cyclohexylmethyl which is optionally substituted by methyl or ethyl.

5. A compound according to claim 1, wherein such compound is 3-(2,4-dichlorobenzyloximino)-2-hydroxy-2-phenyl-1-(1,2,4-triazol-1-yl)-propane of the formula

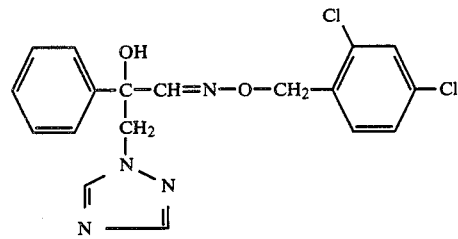

or an addition product thereof with an acid or metal salt.

6. A compound according to claim 1, wherein such compound is 3-(2,4-dichlorobenzyloximino)-3-methyl-2-hydroxy-2-phenyl-1-(1,2,4-triazol-1-yl)-propane of the formula

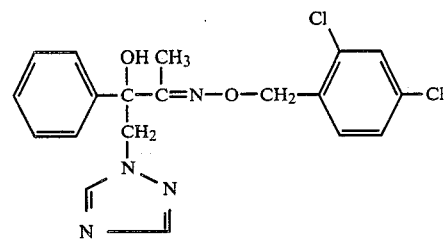

or an addition product thereof with an acid or metal salt.

7. A compound according to claim 1, wherein such compound is 3-(3,4-dichlorobenzyloximino)-3-methyl-2-hydroxy-2-phenyl-1-(1,2,4-triazol-1-yl)-propane of the formula

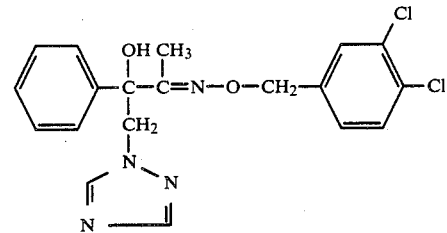

or an addition product thereof with an acid or metal salt.

8. A compound according to claim 1, wherein such compound is 3-(4-chlorobenzyloximino)-3-methyl-2-hydroxy-2-phenyl-1-(1,2,4-triazol-1-yl)-propane of the formula

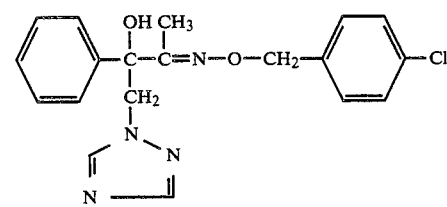

9. A compound according to claim 1, wherein such compound is 3-(4-fluorobenzyloximino)-3-methyl-2-hydroxy-2-phenyl-1-(1,2,4-triazol-1-yl)-propane of the formula

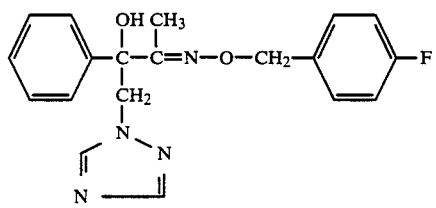

or an addition product thereof with an acid or metal salt.

10. A fungicidal composition comprising a fungicidally effective amount of a compound or addition product according to claim 1 in admixture with a diluent.

11. A method of combating fungi which comprises administering to such fungi or to a fungus habitat a fungicidally effective amount of a compound or addition product according to claim 1.

12. The method according to claim 10, wherein such compound is
3-(2,4-dichlorobenzyloximino)-2-hydroxy-2-phenyl-1-(1,2,4-triazol-1-yl)-propane,
3-(2,4-dichlorobenzyloximino)-3-methyl-2-hydroxy-2-phenyl-1-(1,2,4-triazol-1-yl)-propane,
3-(3,4-dichlorobenzyloximino)-3-methyl-2-hydroxy-2-phenyl-1-(1,2,4-triazol-1-yl)-propane,
3-(4-chlorobenzyloximino)-3-methyl-2-hydroxy-2-phenyl-1-(1,2,4-triazol-1-yl)-propane or
3-(4-fluorobenzyloximino)-3-methyl-2-hydroxy-2-phenyl-1-(1,2,4-triazol-1-yl)-propane,
or an addition product thereof with an acid or metal salt.

* * * * *